(12) United States Patent
Vercruysse

(10) Patent No.: US 10,339,425 B2
(45) Date of Patent: Jul. 2, 2019

(54) SYSTEM AND METHOD FOR CELL RECOGNITION

(71) Applicants: IMEC VZW, Leuven (BE);
KATHOLIEKE UNIVERSITEIT LEUVEN, KU LEUVEN R&D, Leuven (BE)

(72) Inventor: Dries Vercruysse, Sint Andries (BE)

(73) Assignees: IMEC VZW, Leuven (BE);
KATHOLIEKE UNIVERSITEIT LEUVEN, KU LEUVEN R&D, Leuven (BE)

( * ) Notice: Subject to any disclaimer, the term of this patent is extended or adjusted under 35 U.S.C. 154(b) by 135 days.

(21) Appl. No.: 15/503,764

(22) PCT Filed: Aug. 17, 2015

(86) PCT No.: PCT/EP2015/068874
§ 371 (c)(1),
(2) Date: Feb. 14, 2017

(87) PCT Pub. No.: WO2016/024027
PCT Pub. Date: Feb. 18, 2016

(65) Prior Publication Data
US 2017/0270388 A1 Sep. 21, 2017

(30) Foreign Application Priority Data
Aug. 15, 2014 (EP) .................................. 14181204

(51) Int. Cl.
*G06K 9/00* (2006.01)
*G06K 9/62* (2006.01)
(Continued)

(52) U.S. Cl.
CPC ....... *G06K 9/6267* (2013.01); *G01N 15/0205* (2013.01); *G01N 15/0227* (2013.01);
(Continued)

(58) Field of Classification Search
CPC ........... G06K 9/00127; G06K 9/00134; G06K 9/0014; G06K 9/00147; G06K 9/38;
(Continued)

(56) References Cited

U.S. PATENT DOCUMENTS 6,876,760 B1 * 4/2005 Vaisberg .............. G06K 9/0014
382/129
2006/0257013 A1 * 11/2006 Ramm ............... G06K 9/00127
382/133

(Continued)

OTHER PUBLICATIONS

Simon Li, Claudia Buehnemann, Bass Hassan and J. Alison Noble, "Segmentation of Cell Clumps for Quantitative Analysis", IEEE 2010 Annual International Conference of the IEEE Engineering in Medicine and Biology, 2010, pp. 4813-4816.*

(Continued)

*Primary Examiner* — Eric Rush
(74) *Attorney, Agent, or Firm* — McDonnel Boehnen Hulbert & Berghoff LLP

(57) ABSTRACT

The present disclosure relates to systems and methods for cell recognition. At least one embodiment relates to a method for recognizing cell. The method includes receiving an image of the cell. The method also includes performing edge detection on the image of the cell. Further, the method includes detecting ridges within the image of the cell. In addition, the method includes quantifying an internal complexity of the cell by gauging a contrast of the ridges with an average of a Laplacian on the detected ridges.

20 Claims, 12 Drawing Sheets

(51) Int. Cl.
G01N 15/02 (2006.01)
G06T 7/62 (2017.01)
G01N 15/14 (2006.01)
G03H 1/08 (2006.01)
G03H 1/04 (2006.01)
G06T 7/12 (2017.01)
G06T 7/174 (2017.01)
G06T 7/194 (2017.01)
G03H 1/00 (2006.01)
G01N 15/00 (2006.01)

(52) U.S. Cl.
CPC ..... *G01N 15/1463* (2013.01); *G01N 15/1468* (2013.01); *G01N 15/1475* (2013.01); *G03H 1/0443* (2013.01); *G03H 1/0866* (2013.01); *G06K 9/0014* (2013.01); *G06K 9/00127* (2013.01); *G06K 9/00134* (2013.01); *G06T 7/12* (2017.01); *G06T 7/174* (2017.01); *G06T 7/194* (2017.01); *G06T 7/62* (2017.01); *G01N 2015/0065* (2013.01); *G01N 2015/0233* (2013.01); *G03H 2001/0033* (2013.01); *G03H 2001/0447* (2013.01); *G03H 2222/33* (2013.01); *G06K 2209/05* (2013.01); *G06T 2207/10056* (2013.01); *G06T 2207/20224* (2013.01); *G06T 2207/30024* (2013.01)

(58) Field of Classification Search
CPC .... G06K 9/6267; G06K 2209/05; G06T 7/10; G06T 7/12; G06T 7/174; G06T 7/194; G06T 7/60; G06T 7/62; G06T 2207/10056; G06T 2207/20016; G06T 2207/20224; G06T 2207/30024; G03H 1/04; G03H 1/0443; G03H 1/08; G03H 1/0866; G03H 2001/0033; G03H 2001/005; G03H 2001/0447; G01N 15/00; G01N 15/02; G01N 15/0205; G01N 15/0227; G01N 15/10; G01N 15/1429; G01N 15/1431; G01N 15/1434; G01N 15/1436; G01N 15/1463; G01N 15/1468; G01N 15/1475; G01N 15/1484; G01N 2015/0065; G01N 2015/0073; G01N 2015/008; G01N 2015/0233; G01N 2015/025; G01N 2015/03; G01N 2015/035; G01N 2015/1006; G01N 2015/144
USPC ....... 382/100, 108, 128, 129, 133, 134, 173, 382/199, 203, 224, 254, 266, 276, 282, 382/283, 286; 702/19, 21, 23, 29; 356/39
See application file for complete search history.

(56) References Cited

U.S. PATENT DOCUMENTS

| | | | | |
|---|---|---|---|---|
| 2007/0206845 | A1* | 9/2007 | Rao | G06K 9/00127 382/133 |
| 2007/0216906 | A1* | 9/2007 | Javidi | G06K 9/00147 356/457 |
| 2012/0218379 | A1* | 8/2012 | Ozcan | G01N 15/1475 348/40 |
| 2013/0064441 | A1* | 3/2013 | Kask | G06K 9/00147 382/133 |
| 2013/0177935 | A1* | 7/2013 | Di Carlo | G01N 15/1459 435/29 |
| 2013/0230230 | A1* | 9/2013 | Ajemba | G06K 9/00147 382/133 |
| 2013/0315466 | A1* | 11/2013 | Drell | G06K 9/00127 382/133 |
| 2014/0113324 | A1* | 4/2014 | Di Carlo | G06K 9/4604 435/29 |
| 2016/0231225 | A1* | 8/2016 | Hayden | G01N 15/10 |
| 2017/0132450 | A1* | 5/2017 | El-Zehiry | G06K 9/00147 |

OTHER PUBLICATIONS

Jiyan Pan, Takeo Kanade, and Mei Chen, "Learning to Detect Different Types of Cells under Phase Contrast Microscopy", Microscopic Image Analysis with Applications in Biology (MIAAB), 2009, pp. 1-8.*

PCT International Search Report and Written Opinion, PCT International Application No. PCT/EP2015/068874, dated Oct. 29, 2015, 15 pages.

Lindeberg, Tony, "Edge Detection and Ridge Detection with Automatic Scale Selection", Technical Report ISRN KTH/NA/P-96/06-SE, International Journal of Computer Vision, vol. 30, No. 2, 1998, 48 pages.

Nilufar, Sharmin et al., "Learning a Cost Function for Interactive Microscope Image Segmentation", Modern Artifical Intelligence for Health Analytics: Papers from the AAAI-14 Workshops, Jul. 27, 2014, pp. 31-34.

Lindeberg, Tony, "Chapter II, Scale-Space Theory: A Basic Tool for Analyzing Structures at Different Scales", Advances in Applied Statistics, Jan. 1, 1994, pp. 225-270.

Colomb, Tristan et al., "A Complete Digital Optics Applied to Digital Holographic Microscopy: Application to Chromatic Abberation Compensation", Optical Measurement Systems for Industrial Inspection, vol. 6616, Jun. 18, 2007, pp. 1-8.

Smereka, Marcin et al., "Detection of Pathological Cells in Phase Contrast Cytological Images", Advanced Concepts for Intelligent Vision Systems Lecture Notes in Computer Science, Jan. 1, 2006, pp. 821-832.

Meijering, Erik, "Cell Segmentation: 50 Years Down the Road, Life Sciences", IEEE Signal Processing Magazine, vol. 29, No. 5, Sep. 1, 2012, pp. 140, 142-145.

Pinz, Axel, "Object Categorization", Foundations and Trends in Computer Graphics and Vision, vol. 1, No. 4, Jan. 1, 2005, pp. 255-312.

Vercruysse, Dries et al., "Three-Part Differential of Unlabeled Leukocytes With a Compact Lens-Free Imaging Flow Cytometer", Lab on a Chip, vol. 15, No. 4, Jan. 1, 2015, pp. 1123-1132.

Vercruysse, Dries et al., "Three-Part Differential of Unlabeled Leukocytes With a Compact Lens-Free Imaging Flow Cytometer—Supplementary Information", Electronic Supplementary Material (ESI) for Lab on a Chip, Jan. 1, 2015, 8 pages.

Demant, C. et al., "Chapter 7—Gauging", Industrial Image Processing, Springer, Oct. 23, 2013, pp. 173-174.

* cited by examiner

Replacement Sheet

FIG. 21A     FIG. 21B

SYSTEM AND METHOD FOR CELL RECOGNITION

CROSS-REFERENCE TO RELATED APPLICATION

The present application is a national stage entry of PCT/EP2015/068874 filed Aug. 17, 2015, which claims priority to European Patent Application No. 14181204.0 filed on Aug. 15, 2014, the contents of each of which are hereby incorporated by reference.

FIELD OF THE INVENTION

The disclosure relates to particle analysis. More specifically, the disclosure relates to systems and methods for cell recognition.

BACKGROUND OF THE INVENTION

The white blood cell (WBC) differential is one component of the complete blood count (CBC) which can deliver information on a variety of medical conditions including infection, allergic reactions and drug responses. A WBC differential cannot typically be performed at the point-of-care or in an emergency setting, necessitating transfer to an off-site centralized facility in order to be analyzed on conventional hematology analyzers. State-of-the-art analyzers, while highly accurate and capable of simultaneously determining a large number of parameters relating to erythrocytes, leukocytes and platelets, possess a large footprint, require dedicated staff and rely on expensive reagents. Efforts are currently being directed at developing portable hematology analyzers based on label-free technologies that could perform WBC differentials at the point-of-care or in situations where a rapid and accurate analysis is more critical than a more comprehensive but delayed evaluation. Various methods are being explored to engineer such low-cost analyzers using intrinsic cellular parameters such as size, impedance and dielectric properties as separation criteria. Lateral di-electrophoresis and hydrodynamic separation are two recently developed microfluidic techniques, which can separate a particle flow into different size-dependent flows. Both techniques have been used to separate whole blood into platelets, erythrocytes and leukocytes. However, without actively altering the size of either monocytes or granulocytes, a leukocyte differential has remained difficult to achieve. Alternatively, generating a 3-part WBC differential was shown to be possible with impedance spectroscopy. Cell size and internal composition are translated into characteristic impedance signals measurable by electrodes positioned in a microfluidic channel. By performing a dual frequency analysis a 3-part classification of the main leukocyte subtypes was achieved. Lens-free in-line holographic microscopy has emerged as a promising label-free, cell-analysis technique which delivers a cell image by capturing the interference pattern of scattered and transmitted light of a cell directly on a CMOS chip, in the absence of objective lenses and other complex optics. Software-based reconstruction of the interference pattern generates an image of the cell, which retains its morphological signature. Given the relative simplicity of its optical components, lens-free microscopy holds great potential for miniaturization and integration into a microfluidic blood analysis platform that could be used at the point-of-care or in emergency settings.

This technique has already been shown to be compatible with a variety of biological specimens, including blood cells. Wide field-of-view lens-free holographic microscope have been used to capture holograms of cells within a diluted blood sample and showed the reconstructed images of erythrocytes, leukocytes and platelets to be comparable to images captured with a conventional microscope equipped with a 40× objective-lens. Holograms of Wright-Giemsa-stained blood smears were acquired and used the recovered phase and amplitude images to discriminate between the three main leukocyte populations. Albeit not label-free, these measurements pointed to the potential of generating a 3-part WBC differential based on analysis of holographic images. In all these in-line holographic geometries, a large field-of-view configuration is exploited by using plane wave illumination. Reconstructions of holograms taken with a plane wave holographic geometry are typically limited by the camera's pixel pitch. This limit can be overcome by taking multiple images under slightly different angles of the illumination source or with a subpixel shift of the sample or camera. While this configuration is not compatible with imaging fast moving objects such as cells owing in a microfluidic channel, subpixel resolution can still be achieved by using point-source illumination placed close to the object. The spherical wavefront of the point source serves as an at-lens transformation, magnifying the image and increasing the resolution. This point-source, digital, in-line, holographic microscopy (PSDIHM) geometry has been used to image aquatic organisms and to obtain detailed phase information of various cell types.

SUMMARY OF THE INVENTION

Some embodiments provide low-cost, portable cell-analyzers.

Such low-cost, portable cell-analyzers may be provided by a method and device according to disclosed embodiments.

In one aspect, the disclosure relates to a method for recognizing a cell, the method comprising receiving an image of the cell, performing edge detection on the image of the cell, performing ridge detection on the image of the cell, and gauging the contrast of the ridges by the average of the Laplacian on the detected ridges.

It was surprisingly found that accurate detection of cell types for label free cells can be performed based on information obtained when applying the gauging step of the contrast of the ridges with the average Laplacian on the edge. In some embodiments, the lens-free, imaged based classification is in agreement with the 3-part differential generated by a conventional hematology analyzer on the same blood sample. Some embodiments enable granulocytes, monocytes, and lymphocytes to be classified based on a measure which is based on the internal complexity of the cell and on the cell diameter, for example. Some embodiments enable the cell size and the cytoplasmic granularity to be identified using a scale-space based algorithm. Some embodiments enable the internal complexity of the cell to be quantified by gauging the contrast of the ridges with the average of the Laplacian on the detected ridges. Some embodiments enable the leukocyte subtypes to be distinguished based on the morphological features of the subtypes using methods according to the present invention.

Similar results can be obtained as with phase contrast and fluorescence microscopy images as well as with brightfield images of a blood smear.

The method may furthermore comprise performing a scale—space based algorithm and characterizing based thereon an edge and an internal complexity of the cell.

Said characterizing an internal complexity of the cell may comprise characterizing a granularity of the cell.

Receiving an image of the cell may comprise obtaining a hologram of the cell, obtaining a background hologram without a cell which is the background hologram, removing the background from the hologram of the cell using the background hologram, and reconstructing the image of the cell from the hologram of which the background is removed resulting in an image of the cell.

Some embodiments increase the sensitivity and accuracy for detection of cell edges and ridges by removing the background from the cell hologram. Some embodiments use background subtraction to allow the edges of the imaged cell to have more contrast in the amplitude of the reconstruction than without the background subtraction.

Obtaining the image of the cell may comprise removing the background from the image of the cell by fitting a higher order polynomial with the background of image and removing the higher order polynomial from the image.

The image of the cell may be an image of a label-free cell.

When the cell is a leukocyte, the method may comprise selecting, based on at least the ridge information for the image of the cell, a cell type for the imaged cell from one of a granulocyte, a monocyte or a lymphocyte. Some embodiments enable the background of the reconstructed image, also referred to as the virtual image, to be removed without requiring multiple reconstruction steps moving back and forth between the hologram, image and virtual image plane. In embodiments an iteration need not be required for the virtual image removal and therefore the reconstruction algorithm is faster than in cases where multiple iteration steps are required. Therefore, some embodiments enable a decrease in the analysis time.

Said selecting a cell type may be based on a combination of the edge detection results and the ridge detection results. Some embodiments enable cells to be classified based on the combination of the ridge detection results and the edge detection results. Some embodiments, based on numerical reconstruction of the holograms, enable unlabeled leukocytes to be classified into three main subtypes: lymphocytes, monocytes, and granulocytes. Some embodiments, despite the limited resolution of lens-free systems, enable the acquired images to be processed with methods in accordance with embodiments described herein, and thereby display clear differences in size and internal complexity of purified lymphocytes, monocytes, and granulocytes. Some embodiments use two-dimensional histograms of the obtained cell features to discriminate between different leukocyte subtypes. The cell features can be obtained based on analysis of the lens-free images obtained using systems in accordance with certain embodiments. In some embodiments, the classification results of white blood cells is similar to the classification done by a conventional hematology analyzer.

The disclosure also relates to a system for recognition of a cell, the system comprising an input device arranged for receiving an image of the cell; and a processing device configured (e.g. programmed) for performing edge detection on the image of the cell and for performing ridge detection on the image of the cell wherein the processing device furthermore is configured for gauging the contrast of the ridges by the average of the Laplacian on the detected ridges.

The processing device may be configured for performing a scale—space based algorithm and for characterizing based thereon an edge and an internal complexity or granularity of the cell.

The input device may be an image recording device comprises a camera, a microfluidic chip for guiding cells into a detection region of the camera and/or a microfluidic chip holder for holding such a microfluidic chip and a radiation source for stroboscopic illumination of the cell in the detection region.

The processing device may be further configured for identifying a cell type of a cell being a leukocyte, based on at least ridge information for the image of the cell, as one of a granulocyte, a monocyte or a lymphocyte. Certain embodiments enable a lens-free holographic microscope to be used to image and recognize blood cells flowing in a microfluidic chip. Some embodiments are compact, point-source-based, holographic, lens-free imaging systems that they enable image capturing of blood cells inflow by stroboscopic illumination. Some embodiments enable the relative simplicity of the optical components in point-source digital in-line holographic microscopy lends this technology potential for miniaturization and integration into a portable hematology analyzer. An accurate and compact point-of-care hematology device could be used in time-sensitive emergency room situations, as part of ambulance equipment, or in retirement homes. Systems according example embodiments could also potentially serve to shift treatment-based follow-ups such as chemotherapy monitoring, away from centralized hospitals and closer to the doctor's office, decreasing waiting times and improving patient comfort. In some embodiments, the point-source, lens-free imaging technology based on capturing images and using application-specific software analysis to extract relevant features can be used in disease areas, such as for example malaria, that are currently difficult to diagnose in resource-limited settings.

Some embodiments enable an accurate method for identifying a cell to be obtained without labelling of the cells or without significant manipulation of the cells. Some embodiments reduce cellular manipulation. E.g. when considering cells in blood, the blood may be manipulated as little as possible. No use needs to be made of stains, fluorescent markers, media that blow up or shrinks cells or increase their granularity. Minimal manipulation of cells is interesting to make the measured sample still usable and because that way little additional steps need to be taken before measuring the sample.

The disclosure also relates to a computer program product for, when executing on a processing device, carrying out one of the methods as described above.

The disclosure also relates to a data carrier storing the computer program product or to the transmission of the computer program product over a local or wide area network.

The disclosure also relates to the use of a system as described above for identifying a cell type of a leukocyte as one of a granulocyte, a monocyte, or a lymphocyte.

Particular aspects of the invention are set out in the accompanying independent and dependent claims. Features from the dependent claims may be combined with features of the independent claims and with features of other dependent claims as appropriate and not merely as explicitly set out in the claims.

These and other aspects will be apparent from and elucidated with reference to the embodiment(s) described hereinafter.

BRIEF DESCRIPTION OF THE DRAWINGS

FIG. 21A shows a histogram for T-lymphocytes obtained through systems and methods, according to example embodiments.

FIG. 21B shows a histogram for monocytes obtained through systems and methods, according to example embodiments.

Figure 1:
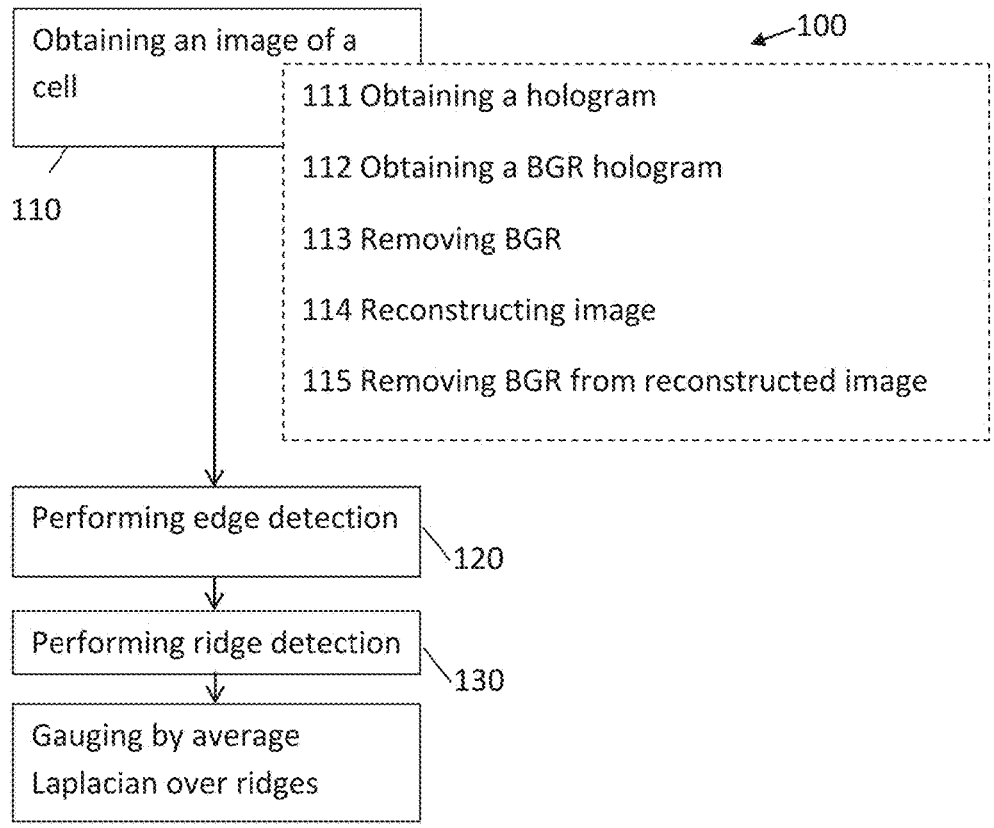
FIG. 1 illustrates a method for recognition of a cell, according to example embodiments.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

Various embodiments will be described with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present embodiment, the only relevant components of the device are A and B.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where, in embodiments disclosed herein, reference is made to "the pinhole", reference is made to the aperture of a lens-free camera. In example embodiments, the hologram of a cell is taken when it is in the detection area, e.g. under the pinhole.

Where, in embodiments disclosed herein, reference is made to "morphological features", reference is made to the cell size and to the cytoplasmic granularity also referred to as the internal complexity of the cell.

Where, in embodiments disclosed herein, reference is made to "gauging" of the contrast of the ridges reference is made to determining or estimating a value for the contrast of the ridges. In various embodiments, such a value is given by the average of the Laplacian on the detected ridges.

In a first aspect, the disclosure relates to a system for recognition of a cell. The system comprises an input device for receiving an image of the cell as well as a processing device for performing edge detection on the image of the cell and for performing ridge detection on the image of the cell, and furthermore gauging the contrast of the ridges by the average of the Laplacian on the detected ridges.

The latter provides a quantification of the internal complexity of the cell. The input device may be a device for receiving an image of the cell. Alternatively, the input device may comprise a device for obtaining/recording cell image information comprising a camera, a microfluidic chip for guiding cells into a position in the field of view of the camera and/or a holder for such a microfluidic chip and a radiation source such as for example a laser light source for stroboscopic illumination of the field of view.

By way of illustration, the present invention not being limited thereto, features and advantages of embodiments of the present invention are further discussed with reference to standard and optional features of particular embodiments and examples.

In some embodiments, the input device comprises hardware for obtaining an image of the cell. The radiation coming from the radiation source 230 may be guided by a waveguide positioned out of plane with respect to the average plane of the microfluidic device and may create a point-source illumination. The waveguide 250 may be part of a separate optical chip. The optical chip may be positioned out of plane. In one embodiment, the edge of the optical chip also defines the radiation outcoupling edge of the waveguide and the edge may be facing the microfluidic chip, e.g. be positioned above the microfluidic chip. Such optical wafers may for example be an optical wafer wherein an optical waveguide is embedded and wherein the wafer are cut such that the cutting edge traverses the embedded waveguide. In example embodiments, the waveguide 250 based point source is situated above the microfluidic chip 220. In some embodiments, the microfluidic chip 220 is placed on top of the camera 210.

In some embodiments that include a camera 210, the camera may be a high speed camera. The high speed camera may comprise a monochrome global shutter CMOS sensor with 2048×2048, 5.5 μm×5.5 μm pixels. In some embodiments, the camera 210 is a high speed camera that can capture motionless holograms of in-flow cells at speeds up to 157 frames per second. Therefore stroboscopic illumination of the field of view is applied.

Figure 2:
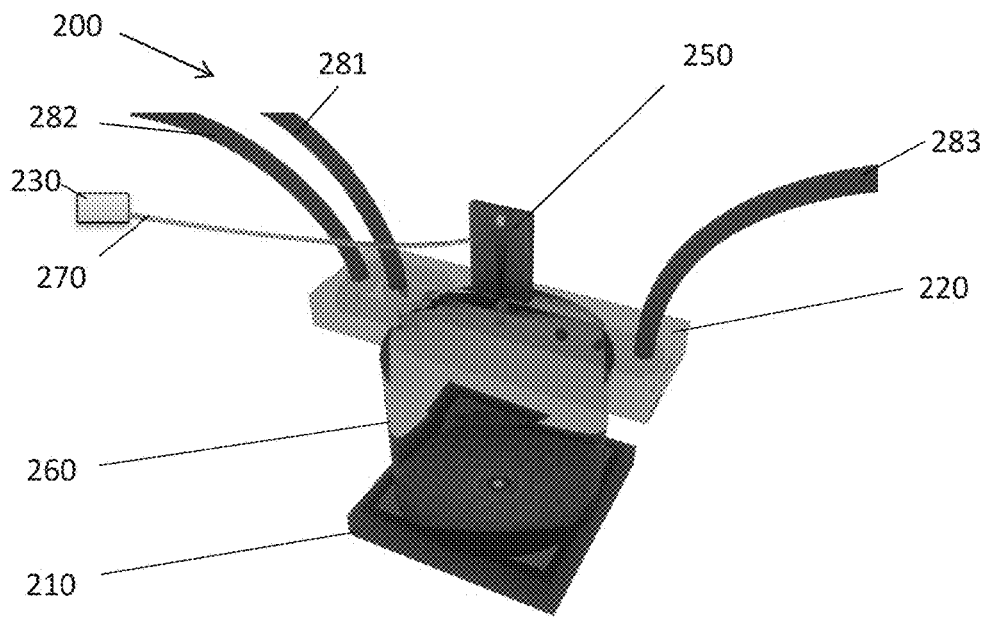
FIG. 2 illustrates a schematic overview of a system for recognition of a cell, according to example embodiments.
Figure 3:
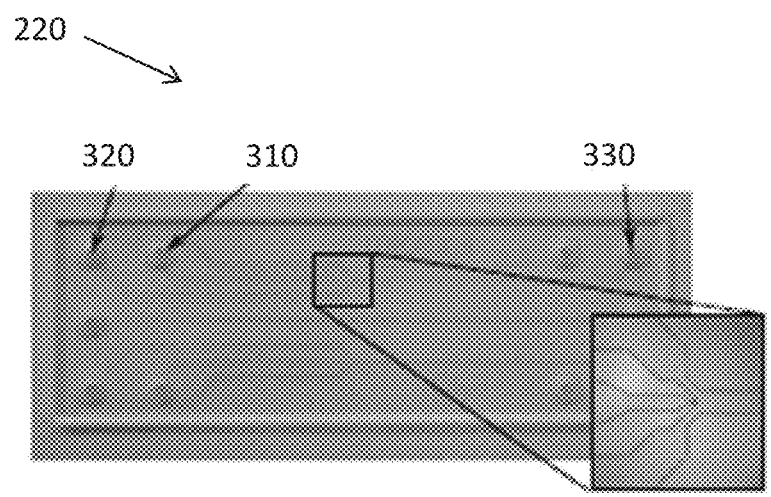
FIG. 3 is a picture of a microfluidic chip, according to example embodiments.

In an example embodiment, the microfluidic chip 220 comprises a substrate in which channels are edged with a depth between 15 μm and 45 μm (between 25 μm and 35 μm, such as 30 μm). The substrate may be made of glass. The substrate may be covered by a glass cover with a thickness of more than 80 μm, e.g. between 80 μm and 170 μm, for example between 100 μm and 160 μm, for example about 130 μm. In some embodiments, tubes are connected with the channels. These tubes may be bonded to the channels of the microfluidic chip through epoxy bonding. In some embodiments a complete semiconductor integrated solution also can be used. An example of the microfluidic chip 220 and the tubes 281, 282, 283 is illustrated in FIG. 2 and in FIG. 3. In the example embodiment of FIG. 2 and FIG. 3 two input tubes and one output tube 283 are present. The first input tube 281 is the tube for transporting the sample into the microfluidic chip 220. It is connected with the input of main channel 310 of the microfluidic chip. The second input tube 282 is the tube carrying the buffer used in the hydrodynamic focusing of the cell sample. It is connected with the buffer channel 320 of the microfluidic chip 220. The third tube is the output tube 283 and it is connected with the output of the main channel 330 of the microfluidic chip 220. In one example microfluidic focusing is used. In certain embodiments, a pump might be connected to both input tubes. The pump puts a pressure of a few tens mBar on the sample and the focusing fluid. The applied pressure will depend on the length and thickness of the tubing. The pressure in the tubes may be regulated such that a stable focused cell flow is generated.

In some embodiments, the waveguide 250 is fabricated from SiN evaporated on a Si substrate having a $SiO_2$ spacer in between. The thickness of the SiN may be between 160 nm and 200 nm (e.g., between 170 nm and 190 nm, such as 180 nm). The thickness of the SiN typically may depend on the wavelength. The thickness of the $SiO_2$ spacer may be between 1 μm and 3 μm, for example between 1.5 μm and 2.5 μm, for example 2 μm. The thickness may be selected such that the optical mode overlaps as little as possible with the substrate. The periodic grating to couple in the laser light, and the waveguide may be patterned on top of the SiN using optical lithography and etched out with a dry etch. After resist removal, an additional layer with a thickness of for example 2 μm may be deposited. The periodic grating may be 5 μm large and may be forming the start of the waveguide. In some embodiments, the periodic grating may taper from 5 μm to 200 nm over a length of 1 mm to produce a single mode waveguide at $\lambda=532$ nm. An exemplary example embodiment of the waveguide 250 is shown in FIG. 2.

In various embodiments, the laser light source 230 is coupled into an optical fiber 270 which may be a polarization maintaining fiber. In example embodiments, the end of the optical fiber 270 is connected perpendicular to the top of the periodic grating of the waveguide 250. The polarization of the out-coupled light from the laser is tuned to match the grating by a half-wave plate before entering the fiber.

Figure 5:
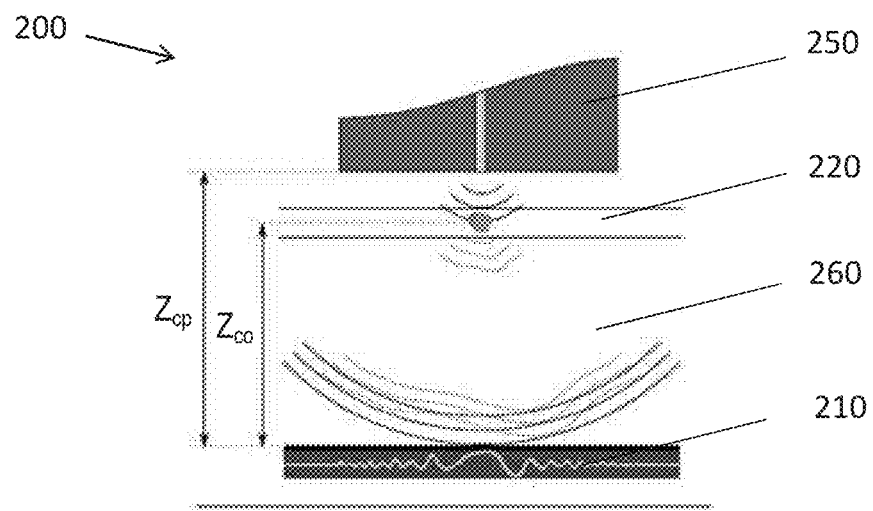
FIG. 5 illustrates a schematic overview of a system for recognition of a cell, according to example embodiments.

FIG. 5 shows a schematic presentation of a system 200 for holographic measurements in accordance with example embodiments. FIG. 5 shows a waveguide 250 for creating a point-source illumination. FIG. 5 also shows a microfluidic chip 220 below the waveguide 250. In some embodiments, the microfluidic chip 250 is a glass microfluidic chip. In some embodiments the microfluidic chip also may be made of a polymer such as PMDS. Alternatively also SU-8 can be used. It is to be noticed that basically any material suitable for creating a microfluidic channel in a chip can be used. FIG. 5 also shows a camera 210. This camera may be an image sensor, e.g. a high speed CMOS camera. In example embodiments, immersion oil and a glass window 260 are placed between the waveguide 250, the microfluidic chip 220 and the camera 210 in order to create a completer refractive index-matched system. Oil may be provided to optically connect the waveguide and the chip. The glass window 260 is also shown in FIG. 2 wherein a system 200 in accordance with an example embodiment is illustrated. FIG. 5 does not show the laser light source 230. This laser light source 230 may be connected via an optical fiber 270 to the waveguide 250. Laser light from the tip of the waveguide creates a point-source-like illumination.

Figure 4:
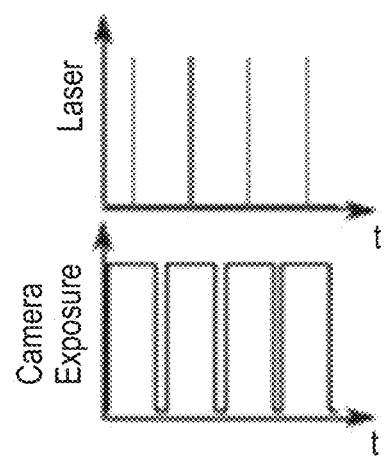
FIG. 4 illustrates a possible timing of stroboscopic illumination and camera exposure, according to example embodiments.

In some embodiments, the microfluidic chip 250 comprises a main channel through which the cells travel. Cells are provided at the input of the main channel 310 and cells are exiting the main channel at the output 330. Cells travelling through the main channel 310 of the microfluidic chip 220 scatter the laser light. The scattered and unscattered light form an interference pattern or hologram. This hologram is captured by the camera 210 positioned below the microfluidic chip 220. In example embodiments, stroboscopic illumination using the laser light source 230 is employed. Some embodiments avoid motion blur, caused by moving cells. In systems where the cells are continuously illuminated motion blur occurs because of the movement of the cells. Some embodiments avoid motion blur by using stroboscopic illumination. A possible timing of stroboscopic illumination and camera exposure is illustrated in the graphs of FIG. 4. The top graph shows the illumination time of the field of view by a nanosecond laser. The bottom graph shows the exposure cycles of the camera. In some embodiments, a nanosecond laser is coupled into the optical fiber 270 and a single laser pulse is applied for each camera exposure cycle. In some embodiments, the cells flow at a speed between 200 µm/s to 4500 µm/s. The optimized speed depends on the frame rate of the camera. In one example, if the cells are for example 5 cell diameters apart and taking into account an average cell diameter of about 10 µm the distance between cells may be about 50 µm and with a framerate of 150 f/s a flow rate of 7500 µm/s may be used. The laser pulse widths are short enough to prevent motion blurring at the given cell flow speed (i.e. the motion blur is well below the resolution of the system, making the image essentially stationary). The pulse width of the nanosecond laser may be between 9 and 20 ns. The pulse width may be longer. It may depend on the flow speed. If one works at a resolution of 500 nm one does not want more than 250 nm movement blur. Taking into account a flow speed of 7500 µm/s, the pulses may be shorter than 33 µs.

In a second aspect, the disclosure relates to a method for recognizing a cell.

In some embodiments, in a first step 110 an image of a cell is obtained. The image of the cell may be obtained by recording a hologram of the cell and by numerically reconstructing the image of the cell from the hologram of the cell.

In example embodiments, the resulting reconstruction is further analyzed by performing edge detection 120 and ridge detection 130. Thereby, typically the cell size and the internal complexity of the cell may be measured. This is done in a second step 120 and a third step 130.

In the second step 120 edge detection is performed on the image of the cell and in the third step 130 ridge detection is performed on the edge of the cell. The contrast of the ridges is gauged by the average of the Laplacian on the detected ridge(s). The latter is a measure for the quantification of the internal complexity of the cell.

In certain embodiments, a measure is thus defined for distinguishing the cells based on their morphological differences. This measure is quantified by a scale-space edge and ridge detection analysis on the phase and amplitude of the reconstruction and a quantification of the contrast. Therefore, in some embodiments, the cellular size and internal complexity is evaluated using a scale-space recognition analysis.

Figure 6:
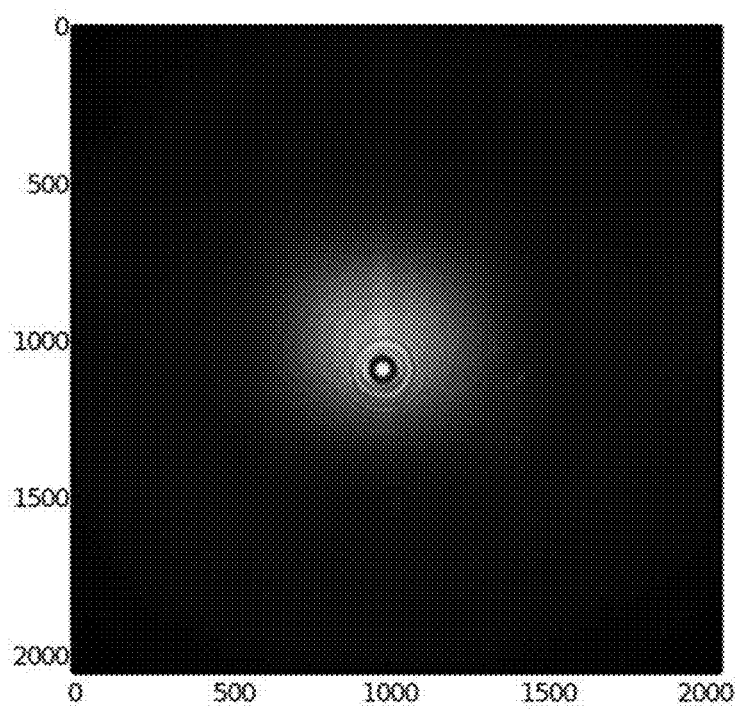
FIG. 6 depicts a raw hologram of a cell taken with a system, according to example embodiments.

In embodiments where the image is not received directly but obtained through a combination of recording and processing or processing alone (if the recording was already done separately), obtaining 110 the image of a cell may be subdivided in a number of processing steps. By way of example, one set of possible processing steps is indicated in the following, embodiments of the present invention not being limited thereto. In process step 111 the image of a cell is obtained. An example thereof is shown in FIG. 6. FIG. 6 depicts a raw hologram taken with a system 200 in accordance with an example embodiment. The hologram of a cell is taken with a high speed camera 210 when the cell is positioned in the detection region. If a pinhole is used in the camera for detecting, the cell may be positioned under the pinhole.

In process step 112 a background hologram is obtained. This hologram is captured under the same conditions as the cell hologram, but as it does not contain a cell, it consequently serves as background. It need not be required to take a background hologram for each cell hologram. The background hologram may be reused as long as the system 200 parameters are not changed. An example of a background hologram is shown in FIG. 7.

Figure 7:
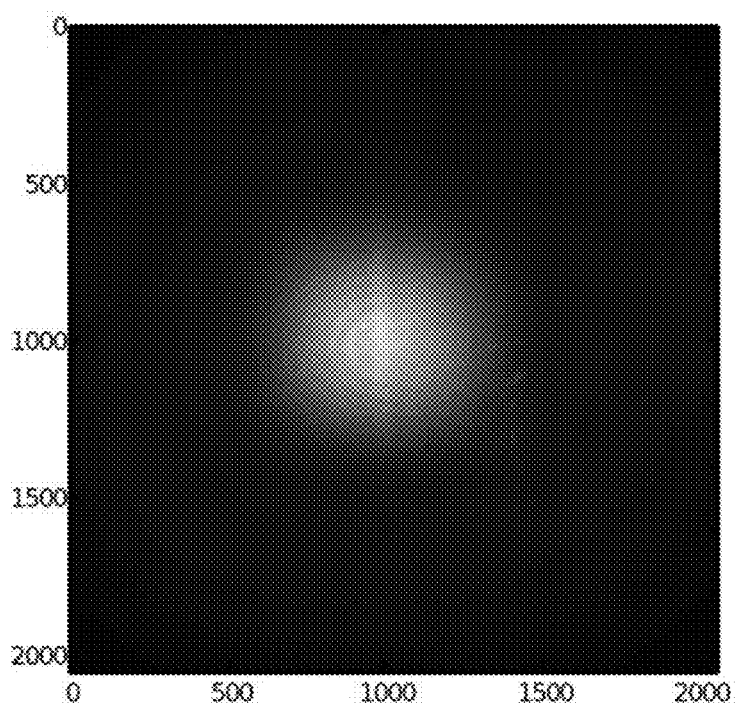
FIG. 7 depicts a background hologram taken with a system, according to example embodiments.

A faint vertical line runs through both images shown in FIG. 6 and FIG. 7. This corresponds to the laminar flow generated by the central hydrodynamic focusing channel (the main channel) of the microfluidic chip 220 which delivers the blood cells, and is triggered by a small difference between the refractive index of sample-containing medium and the focusing medium. All cells follow this line, as is depicted in FIG. 6.

In process step 113 the background is removed from the cell hologram using the background hologram. In various embodiments, the background hologram is subtracted from the cell hologram and the resulting hologram is normalized. In some embodiments, the normalization is done by dividing the background-subtracted image by the value of the background at the maximum of the hologram. In some embodiments, the normalized image is subsequently cropped around the central maxima of the fringe pattern. In certain embodiments, the resulting hologram has 1024 by 1024 pixels. In the example, the background hologram of FIG. 7 is subtracted from the cell hologram of FIG. 6, and after normalization and cropping this results in the hologram of FIG. 8.

In some embodiments, a background image consisting of a hologram without any cell in the detection region, is captured and subtracted from the cell hologram before reconstruction.

In a reconstructing step 114 the image of the cell is reconstructed from the hologram of the cell captured by a camera 210. In some embodiments, the background may be removed from the hologram of the cell and/or the hologram may be normalized, and/or the hologram may be cropped. In the reconstructing step 114 the hologram is numerically diffracted back to the channel plane. The channel plane being the plane of the main channel wherein the cell is moving.

In some embodiments, numerically diffracting back the hologram to the channel plane may be done by using the angular spectrum approach. Using the angular spectrum approach it is possible to do the reconstruction with one fast Fourier transformation on the hologram and one inverse fast Fourier transform on the product of the resulting transformation and the angular spectrum transfer function (the spectral algorithm approach of the Rayleigh-Somerfield integral):

$$U = \mathcal{F}^{-1}\left\{\mathcal{F}\{H\} \cdot e^{\frac{i2\pi d}{\lambda}\sqrt{1-m^2-n^2}}\right\}$$

with H, the captured hologram, d, the reconstruction depth and m and n the spatial frequencies. The spherical reference wavefront is not present in this equation. Since the reference and the impulse response are the same in this transformation they can be combined. As a consequence the reconstruction depth, d, is not a physical distance but rather, $$d = \left(\frac{1}{z_{cc}} - \frac{1}{z_{cp}}\right)^{-1},$$

a combination of $Z_{cc}$ and $Z_{cp}$. $Z_{cc}$ represents the distance from the camera to the pinhole. $Z_{co}$ represents the distance from the camera to the sample. $Z_{cp}$ represents the distance from the camera to the output of the waveguide (i.e. the point source). Reconstructing in this manner also induces a magnification, $$\frac{z_{cp}}{z_{cp} - z_{oc}}.$$

For example a small $Z_{cp}$-$Z_{co}$ and thus a large magnification is used. In such an example, the distance may be limited if a coverslip is used. It typically may be between 150 μm to 200 μm. The distance to the camera $Z_{cp}$ may be 3 to 5 mm. In some embodiments this may be respectively 10 μm to 20 μm and 1 mm, or even shorter. In example embodiments, the point source (the output of the waveguide 250) may be positioned several millimeters above the microfluidic chip 220.

Figure 8:
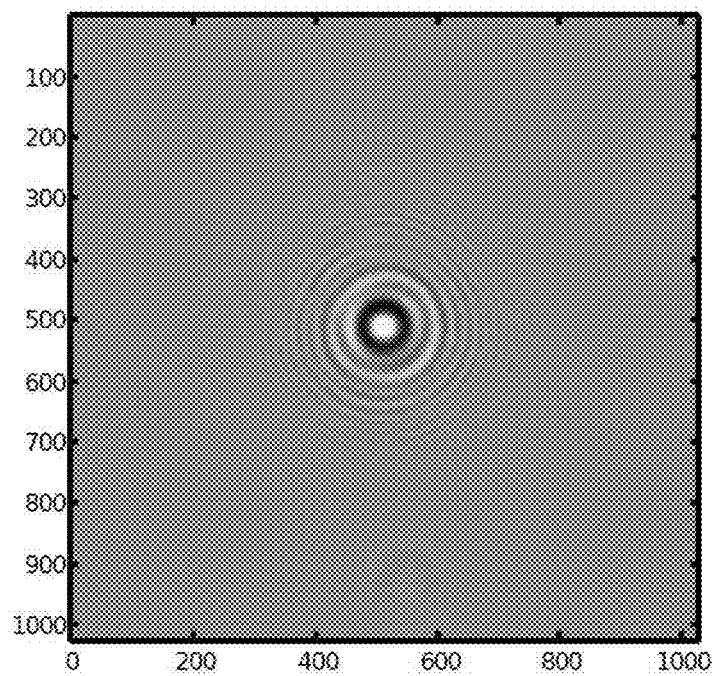
FIG. 8 depicts a hologram of a cell after background removal, normalization, and cropping, according to example embodiments.
Figure 9:
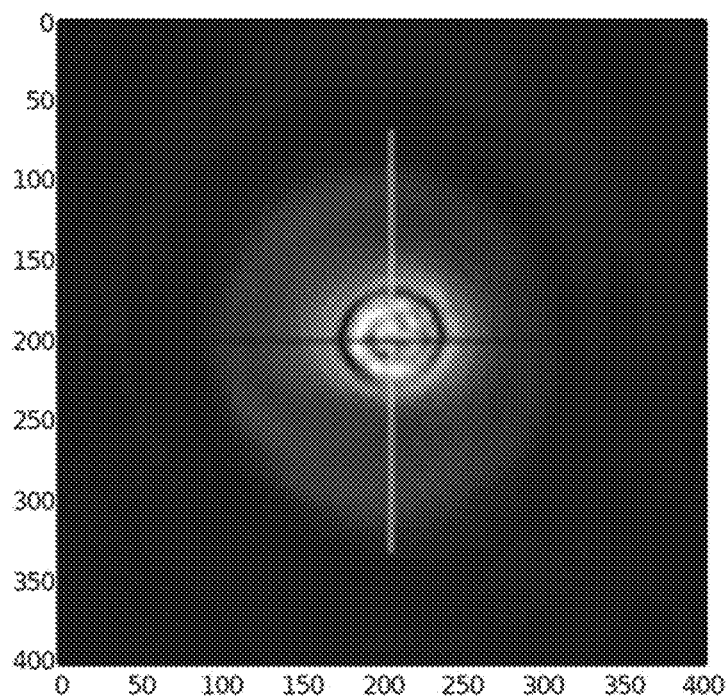
FIG. 9 depicts the amplitude of the reconstruction of the hologram of FIG. 8, according to example embodiments.
Figure 10:
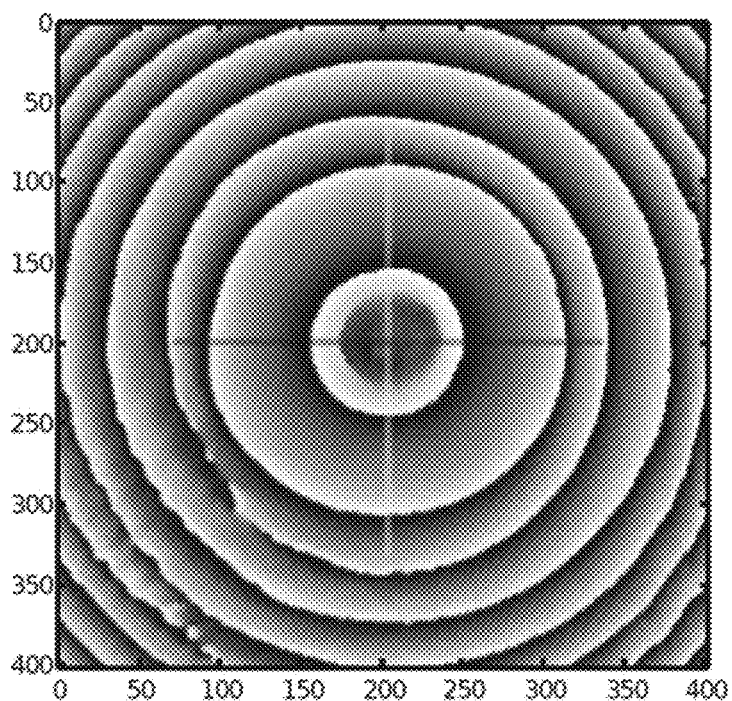
FIG. 10 depicts the phase of the reconstruction of the hologram of FIG. 8, according to example embodiments.

FIG. 9 represents the amplitude of the reconstruction of the hologram of FIG. 8. FIG. 10 represents the phase of the reconstruction of the hologram of FIG. 8. In the reconstructions represented in FIGS. 9 and 10, the cell is clearly detectable in both images although the concomitant presence of the virtual image diminishes the clarity. This extra fringe pattern can be observed in the background of the amplitude image (FIG. 9) and in the background of FIG. 10 as a phase well.

In certain embodiments, no cells are present in the focusing medium in the buffer channels 320 at both sides of the main channel, and the cell concentration is low enough so that there is typically only one cell passing in the field of view at a time.

In some embodiments, obtaining 110 the image of the cell comprises removing the background from the reconstructed image of the cell. This is also referred to as virtual image removal. In some embodiments, the background of the reconstructed image of the cell is removed by fitting a higher order polynomial with the background of the reconstructed image and by removing the higher order polynomial from the reconstructed image. The polynomial may be a fourth order, fifth order or even higher order polynomial.

Although a number of sets of processing steps are possible for obtaining the reconstructed image, the above described process whereby the image of the cell is reconstructed by removing the background by removing a higher order polynomial fitting, e.g. a fourth order polynomial or higher order polynomial, is efficient and allows reconstruction without iterative process. In one aspect, the disclosure therefore also relates to a method and system for obtaining a reconstructed image of a cell by obtaining an image of a cell, fitting a function providing a local minimum to the background, e.g. a fourth order or higher order polynomial to the background, of the image and removing by subtracting it from the reconstructed image.

Figure 11:
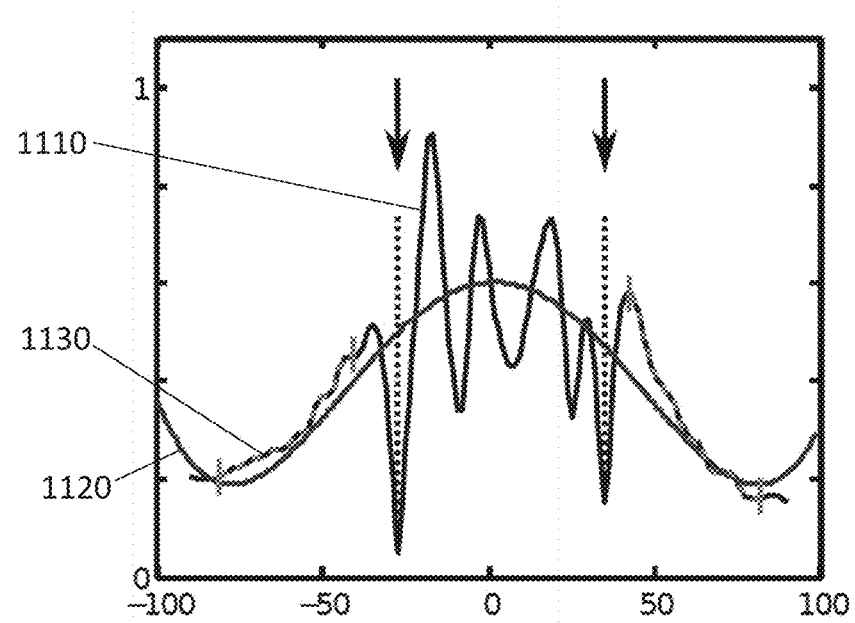
FIG. 11 shows a 2D cross-section of the reconstructed image of FIG. 9, according to example embodiments.
Figure 12:
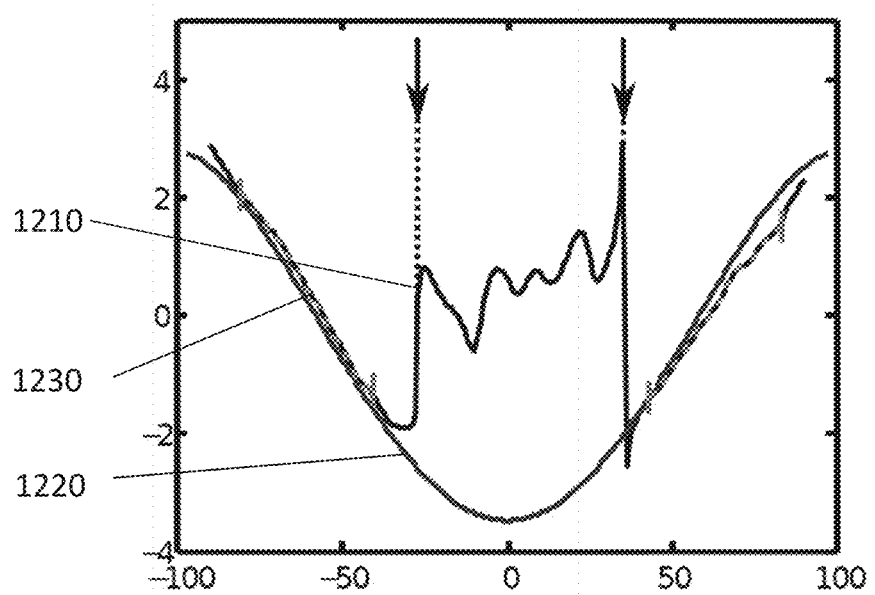
FIG. 12 shows a 2D cross-section of the reconstructed image of FIG. 10, according to example embodiments.
Figure 13:
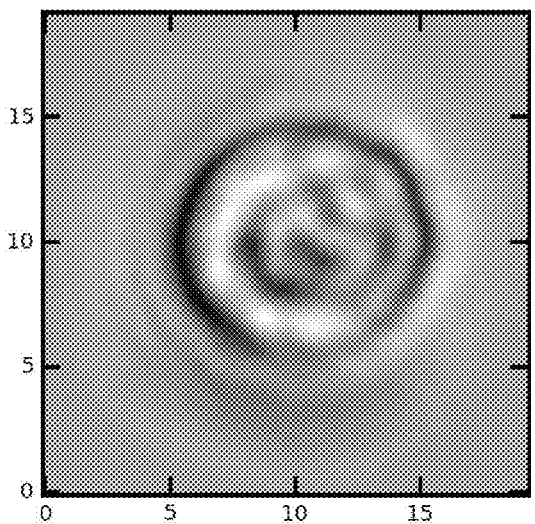
FIG. 13 depicts the difference between the amplitude of the reconstruction and the fit for the amplitude, according to example embodiments.
Figure 14:
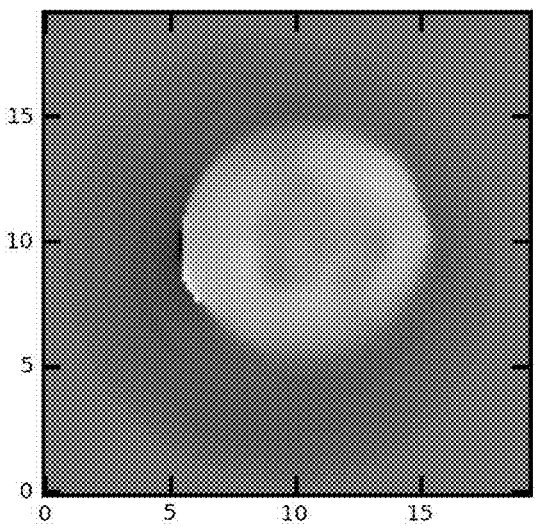
FIG. 14 depicts the difference between the phase of the reconstruction and the fit for the phase, according to example embodiments.

In example embodiments, an estimate of the virtual image is made based on the fringe pattern outside the cell. In an example embodiment, the virtual image is removed by fitting a 2D fourth order polynomial through points outside the cell of the 2D cross-section of the reconstructed images of FIG. 9 and FIG. 10. An example of these cross sections is shown in FIG. 11 for the amplitude and FIG. 12 for the phase. In FIG. 11 the amplitude 1110 is shown and in FIG.12 the phase 1210 is shown. The lines 1130 and 1230 represent the points used for the fit, and they lie outside the cell border indicated by the vertical dashed black line and arrows. The curves 1120 and 1220 are fourth order polynomials fitted on the lines 1130 and 1230. The difference between the reconstruction and the fit for the amplitude and phase is shown in FIG. 13 and FIG. 14, respectively. In FIG. 13 and FIG. 14. the fitted region is shown.

In FIG. 13-16 the axes units are micrometers.

In some embodiments, the system 200 is calibrated by acquiring several images of a central microfluidic focusing channel (the main channel) at different pinhole heights, corresponding with different $Z_{cp}$. Based on the known width of the main channel, the size of the pixel pitch in the reconstruction is linked to the reconstruction dept. In some embodiments, a linear fit through the points representative of the pixel pitch as function of the reconstruction depth. With this fit, one thus can find the pixel pitch corresponding with a certain reconstruction depth. In some embodiments, distances in the reconstruction can be measured. This can be done by calibrating the system 200 as described above.

Figure 17:
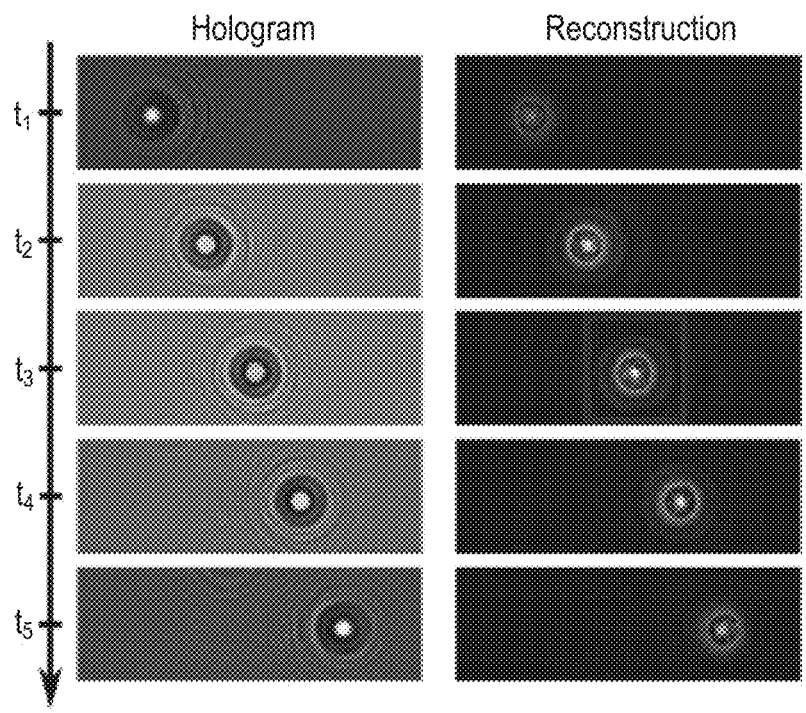
FIG. 17 shows five consecutive holograms and their corresponding reconstruction, according to example embodiments.

In the example of FIG. 17 five consecutive holograms of the same cell are shown. These holograms are taken by a system 200 in accordance with an example embodiment. The left column of FIG. 17 shows five consecutive holograms of the same cell flowing through the main channel of the microfluidic chip 220 in the field of view of the camera 210. The images are taken at 70 frames per second, with the cell moving at approximately 1150 µm/s. The right column of FIG. 17 displays the corresponding reconstructions of the holograms achieved by a method in accordance with example embodiments.

In some embodiments, the quality of the reconstruction is highest when the cell is positioned precisely under the pinhole. An example thereof is illustrated in FIG. 17. In some embodiments, further processing is only done on holograms of cells taken in this region. This region is indicated by a square in FIG. 17 (third row, right column).

Figure 18:
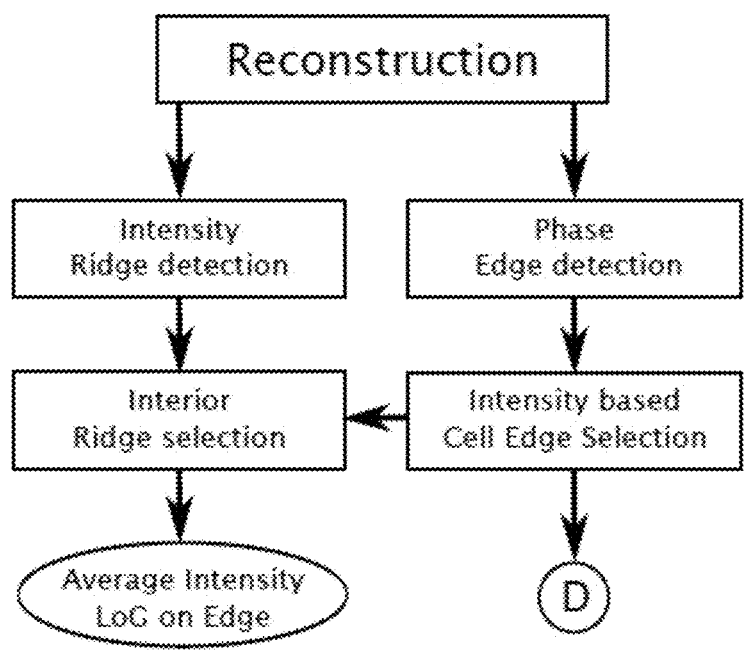
FIG. 18 shows methods steps for obtaining edges and ridges, according to example embodiments.

After obtaining 110 an image of the cell, also referred to as the cleaned-up image, in example embodiments, the cell size and internal complexity is derived by performing a scale-space analysis on the cleaned-up image. In some embodiments, a scale space analysis is applied to locate the cell edge and estimate its internal complexity. In the scale-space analysis the analyzed image may be smoothed by a Gaussian prior to applying a recognition operator. FIG. 18 shows possible method steps for the edge and ridge detection. After obtaining 110 the image of a cell (i.e. the reconstruction), the ridges are detected based on the reconstructed amplitude image and the edges are detected based on the reconstructed phase image. Based on the selection of the cell edge only the ridges internal to the cell are used for further processing. The cell diameter is given as D and determined by fitting a circle through the cell edge. The average intensity LoG relates to the average values of the Laplacian on the ridges. LoG thereby refers to the Laplacian of the Gaussian, as the Laplacian may be applied to the reconstruction after a Gaussian smoothening has been performed. In one example, such a Gaussian smoothening may be performed with sigma (of t) being 250 nm.

In some embodiments, the cell edge is found by performing edge detection 120 on the image of the cell. Edge detection might for example be applied on the phase of the reconstruction as illustrated in FIG. 18. Thereby an edge is defined as a zero-crossing of the second-order directional derivative of the Gaussian smoothed phase. The standard deviation of the Gaussian or scale parameter, t, may be chosen between 3 µm and 8 µm, e.g. between 4 µm and 6 µm, e.g. 5 µm so as to only recognize large edges. In some embodiments, the average image amplitude is calculated along every edge, for all the edges created by this definition. The edge detection thus is performed for defining the cells outline and e.g. for gauging its size.

In some embodiments, the standard deviation of the Gaussian is a measure of the smoothing and determines the size of the detected features in the image. It is therefore also called the scale parameter. In an example embodiment, the operator applied to find edges is the second local derivative. The zero-crossing of this derivative is considered an edge. In some embodiments, only the zero-crossings are relevant and therefore the edge condition can be simplified to an expression which only contains partial derivatives in the xy-system (the xy coordinate system can be oriented in any direction, as there is no preferred direction. In one example the image columns can be used as y and the rows as x):

$$L_x^2 L_{xx} + 2L_x L_y L_{xy} + L_y^2 L_{yy} = 0$$

with $L^x$ and $L^{xx}$, the first and second partial derivative in the x-direction, with $L_y$ and $L_{yy}$, the first and second partial derivative in the y-direction, and with $L_{xy}$, the partial derivative in x- and y-direction. In order to find the cell edge, in example embodiments, this method is applied on the phase image.

Figure 15:
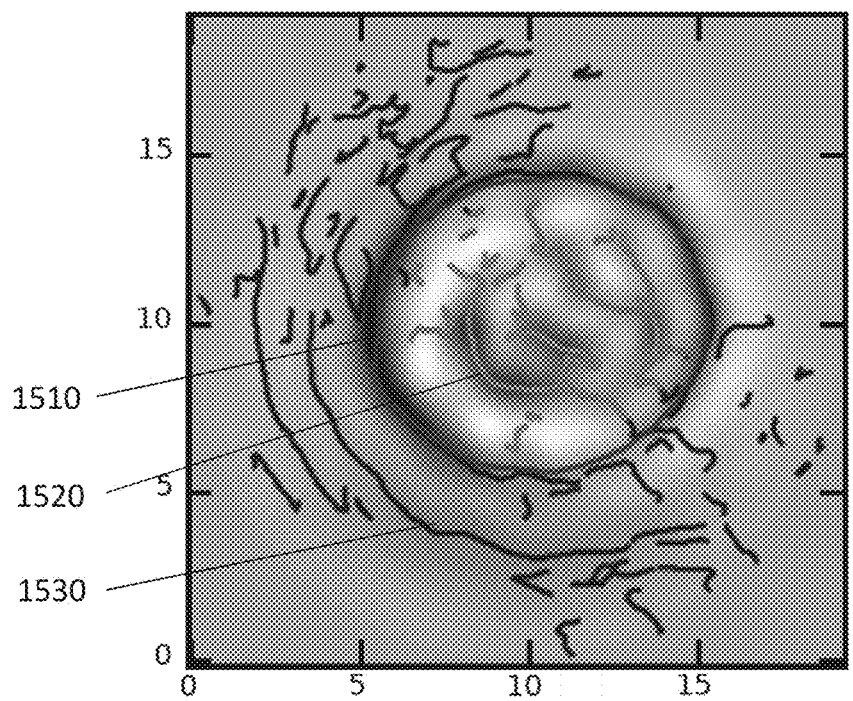
FIG. 15 depicts the detected edges and ridges on the reconstructed image of FIG. 13, according to example embodiments.
Figure 16:
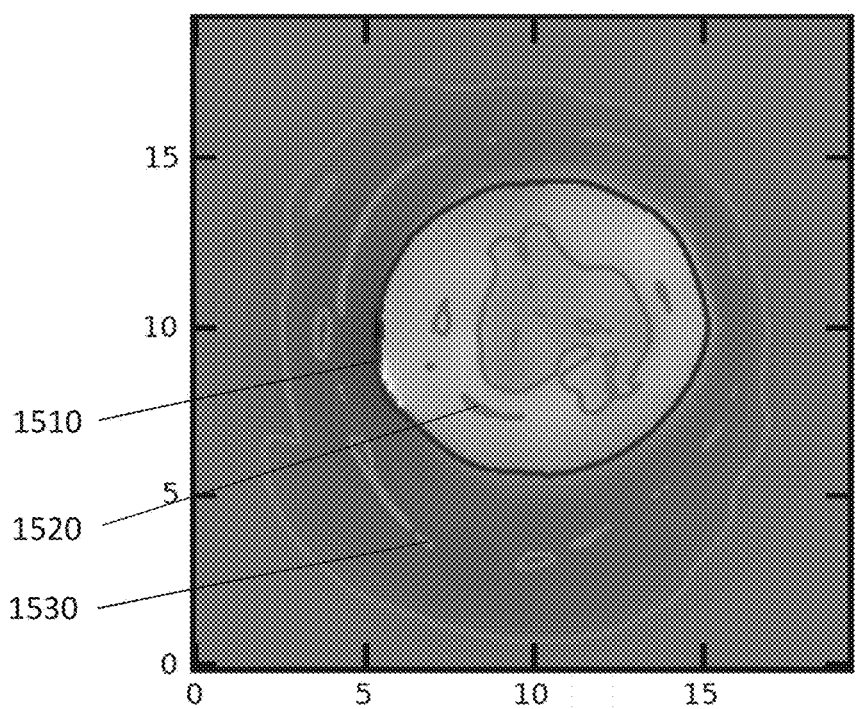
FIG. 16 depicts the detected edges and ridges on the reconstructed image of FIG. 14, according to example embodiments.

For the example hologram of FIG. 6 the detected edges are shown in FIG. 15 and FIG. 16. FIG. 30 shows the amplitude image and FIG. 16 shows the phase image. The cell edge 1510 and the ridges 1520, 1530 are visible in both graphs. The scale parameter applied in this example is 5 µm, since the target structure, a cell, is large. The average intensity over each edge is subsequently calculated. The edge with an average diameter between 5 and 11 82 m with the lowest average reconstruction amplitude value over the edge is labeled the cell edge. The diameter D of a circle fitted through this edge is the cell diameter.

For the internal complexity, the ridges inside the cell edge need to be detected 130. A ridge is defined as a zero-crossing in a first-order local derivative. This condition can be formulated as follows:

$$\begin{cases} L_q = 0 \\ L_{qq} < 0 \\ L_{qq} \geq L_{pp} \end{cases}$$

with $L_q$ and $L_{qq}$, the first and second local derivative in the local q-direction, with $L_{pp}$ the second local derivative in the p-direction and with the pq-system the local coordinate system. The local coordinate system may be as described in Lindeberg, technical report ISRN KTH/NA/P-96/06-SE, Int. J. of Computer Vision, vol. 30, No. 2, 1998. The ridges 1520, 1530 detected in the intensity images are depicted in FIG. 15. In example embodiments, the internal complexity, corresponding with the ridges 1520 inside the cell, is only evaluated inside the cell edge. Once identified, the internal complexity is evaluated by the contrast of the internal ridges which is gauged by the average of the Laplacian on the ridge.

In other words, the algorithm is as follows. First the algorithm detects the ridges. This can for example be done based on a scale space analysis. Such a scale space analysis may use the logarithm of the Laplacian of a Gaussian for filtering out features of a certain size. This results in the ridge, i.e. lines within the cell. Thereafter, the algorithm quantifies the contrast of the ridges. The latter is performed by using the Laplacian or a function thereof, e.g. the average of the Laplacian on the detected ridges, as a size for the contrast in the cell.

Figure 19:
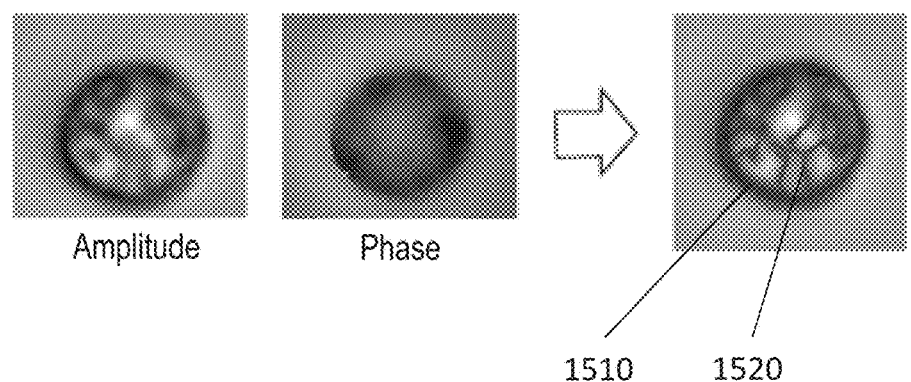
FIG. 19 depicts in the left image the amplitude of the reconstruction, in the middle image the phase of the reconstruction and in the right image the features of the cell obtained through a method, according to example embodiments.

In the example shown in FIG. 19 the left image shows the amplitude of the reconstruction, the middle image shows the phase of the reconstruction and the right image shows the features of the cell obtained through a method in accordance with example embodiments. The features of the cell are derived based on the edge detection 120 and on the ridge detection 130 and on the quantification of the internal complexity by gauging the contrast of the ridges with the average of the Laplacian on the detected ridges. The cell shown in FIG. 19 is a granulocyte. In the example shown in FIG. 19 it can be seen that the cell edge is typically characterized by a low amplitude.

In some embodiments, the contour with the lowest average amplitude is recognized as the cell edge. Edge is used for the cell edge on the phase images, ridges for the complexity on the amplitude image. The diameter of the cell can be derived by fitting a circle through this contour.

In some embodiments, ridge detection 130 is applied on the image of the cell, and the contrast of the ridges is gauged by the average of the Laplacian on the edge, to be used as a quantification of the internal complexity of the cell. Thus, once its edge is known, the internal complexity, or level of cytoplasmic granularity, of the cell can be evaluated through ridge detection 130.

Higher cell internal complexity manifests as more sharply defined ridges inside the cell. This is gauged by averaging the value of the Laplacian of the Gaussian smoothed amplitude images on ridges detected within the cell. In some embodiments, ridges are defined as the zero-crossing of the first-order local directional derivative of the Gaussian smoothed phase image where second-order local directional derivative is higher than zero, since boundaries manifest as minima. In some embodiments, for the ridge analysis, the scale parameter is taken low, for example smaller than 400 nm (e.g., smaller than 300 nm, such as t=250 nm), in order to detect the finer ridges.

In FIG. 19 the amplitude and phase of a reconstructed granulocyte is depicted on the left side. On the right side, the recognized cell edge 1510 and internal edges (ridges) 1520 are visible.

In some embodiments, batches of specific cell types are run through the system 200 in order to build up image libraries of each cell type. These may be stored in a data carrier and used for correlation purposes. The actual recognition may be performed using information of a known set of data. In other words, some calibration may for example be used and recognition may be performed by comparing to calibration data.

In example embodiments, the size of a cell is obtained by measuring the diameter of the edge of the cell. The edge is obtained by performing edge detection 120 on the image of the cell. The internal complexity is quantified by performing ridge detection 130 on the image of the cell, and gauging the contrast of the ridges by the average of the Laplacian on the detected ridges.

In some embodiments, the edge detection and cell information results and the ridge detection and internal complexity results are combined which enables the classification of cells. In example embodiments, the size of the cells and the internal complexity of the cells are represented in a size-complexity scatter plot. In example embodiments, this is applied to white blood cells allowing to differentiate between lymphocytes, monocytes and granulocytes.

In an example, purified fractions of the three main leukocyte subtypes are run through a system 200 corresponding with example embodiments.

In an example 3-part classification is done on a whole blood sample using a system 200 and a method 100, according to example embodiments. Some embodiments enable similar results to be obtained as compared with a conventional 3-part white blood cell differential generated by a Beckman Coulter LH-750 hematology analyzer.

In an example monocytes, and T-lymphocytes are isolated from peripheral blood obtained from healthy persons.

In another example granulocytes are isolated from peripheral blood obtained from healthy persons.

In yet another example the whole blood sample of a healthy person was processed to obtain cell pellets predominantly comprising leukocytes.

As indicated above, the identification of cells may be used for sorting cells, e.g. separating cells. Different mechanisms for sorting cells are known to the person skilled in the art.

Figure 20:
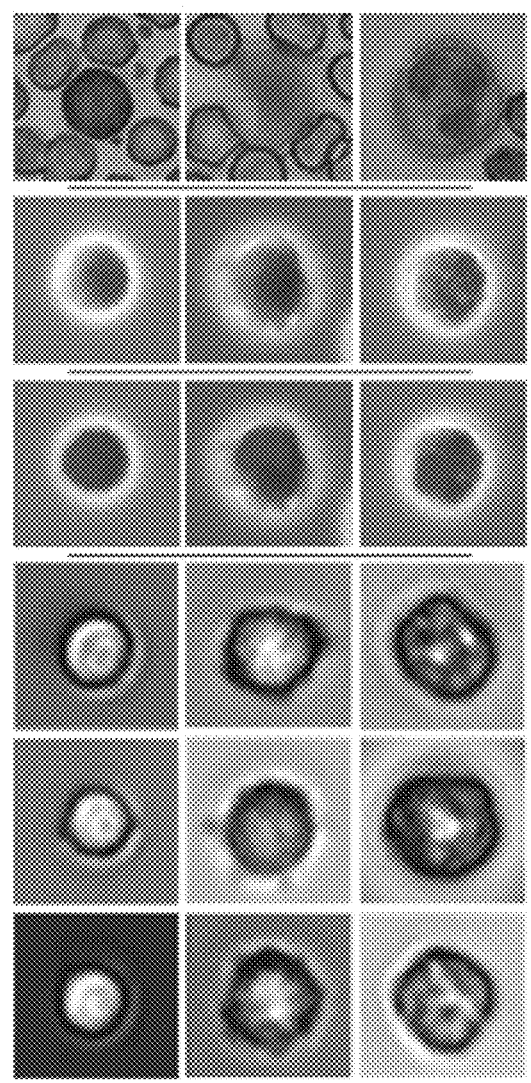
FIG. 20 compares holographic reconstructions made by systems and methods, according to example embodiments with images obtained through alternate imaging techniques.

In the example illustrated in FIG. 20 holographic reconstructions made by systems and methods according to example embodiments are compared with images obtained through conventional imaging techniques. Purified fractions of lymphocytes, monocytes and granulocytes are imaged with the conventional imaging techniques and samples from the same cell preparation are imaged using a system according to example embodiments. The first, second, and third columns of FIG. 20, respectively, represent lymphocytes, monocytes, and granulocytes.

Images of the three types of leukocytes are captured from a conventional Wright-Giemsastained peripheral blood smear of the same sample with brightfield microscope. 3 µl of anticoagulated whole blood was placed on a glass microscope slide and spread onto the surface with another slide at a 45° angle. The sample was thoroughly air-dried at room temperature and stained with Accustain Modied Wright-Giemsa Stain (Sigma-Aldrich) according to manufacturer's guidelines. The slide was examined with an inverted Zeiss Primo Vert microscope at 40× magnification. Cell images were recorded with a Sony Cybershot DSC-W3 camera at 3× optical zoom. These images are shown in the first row of FIG. 20. Cells in the blood smear exhibit characteristic morphologies. A condensed nucleus occupying most of the cytoplasm is clearly visible in the lymphocytes, monocytes display the typical kidney bean-shaped nucleus, and granulocytes reveal the common multilobed (segmented) nucleus (first row of FIG. 20).

Phase contrast and Hoechst-stained fluorescence images of the same cell fractions in suspension were obtained with a widefield fluorescence microscope equipped with a phase contrast module. More specifically, the second and third row of FIG. 20 are obtained as follows: aliquots of purified granulocytes, monocytes and T-lymphocytes are incubated with Hoechst 33342 (Life Technologies) at a final concentration of 5 µg/ml. The mixtures are incubated 20 minutes at room temperature in the dark, washed twice, fixed in 0:5% paraformaldehyde/sucrose, and resuspended in MACS buffer. A 10 µl drop of each mixture was pipetted on a glass microscope slide and cell images were acquired at 100× magnification with an Olympus CellR epi-fluorescence microscope equipped with a phase contrast module, using the corresponding filters.

The last three rows of FIG. 20 show holographic reconstructions (i.e. reconstructed images) of purified leukocytes traveling in-flow, taken with an imaging system 200 in accordance with example embodiments.

While blood smears represent the universally accepted format to observe blood cells under a microscope, it is important to emphasize that the smearing process and the surface tension of the glass slide tends to flatten and stretch cells out, thereby increasing their effective size. Moreover, the air-drying step included in the smear preparation tends to alter the refractive index of cellular components, increasing contrast between nucleus and cytoplasm. Consequently, morphological differences between leukocytes are expected to be much less pronounced in reality than they appear in a smear.

Although the resolution of the holographic reconstructions according to example embodiments may be lower than the microscopy images, similar morphological features can be observed. In the example of FIG. 20 there are clear size differences between lymphocytes and the other leukocytes. In the example of FIG. 20 lymphocytes appear smaller than granulocytes and monocytes in both phase contrast (the second row of FIG. 20) and holographic images (the last three rows of FIG. 20). In the example of FIG. 20 the overall nuclear shape is more difficult to discern in the suspended cells, particularly when the nucleus is unlabelled. Labelling the nucleus with Hoechst improves the nuclear outline (the third row in FIG. 20), albeit not to the level observed in a blood smear, which is expected from spherical, freely-moving cells in solution. Although no visible size differences were observed between granulocytes and monocytes in the holographic reconstructions, the morphologies of their cell surfaces appeared to be slightly different. The cell surface of the granulocytes was smoother than the monocytes which displayed a more ruffled appearance (the last 3 rows in FIG. 20). This effect is also visible in the phase contrast images of the same cell preparations (the second row in FIG. 20), and may ultimately be a consequence of the cell isolation process. An additional discriminating feature between granulocytes and monocytes observed only in the holographic reconstructions is a higher level of internal complexity in the granulocytes (the last 3 rows in FIG. 20). This results in the presence of more defined ridges within the granulocyte cytoplasm, compared to the monocyte cytoplasm which appears less coarse.

Some embodiments enable both the cell size, as well as the cytoplasmic granularity (also referred to as the internal complexity), to be quantified, and that these quantifications are sufficient for discriminating the different leukocyte subtypes.

In an example the purified fractions of each cell type were separately run through a lens-free imaging platform in accordance with example embodiments. The resulting 1000-2000 individual cell image libraries were analyzed with the scale-space based recognition software according to example embodiments. Some embodiments enable a systematic quantification of the morphological features.

Figure 21C:
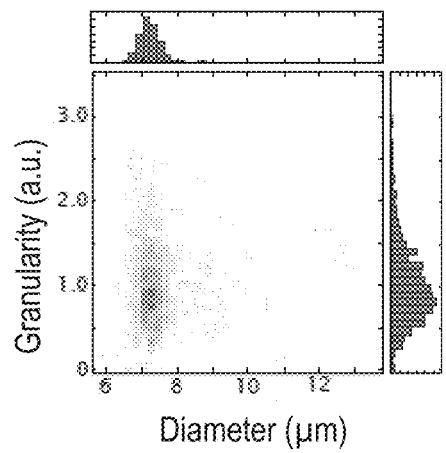
FIG. 21C shows a histogram for granulocytes obtained through systems and methods, according to example embodiments.
Figure 21C:
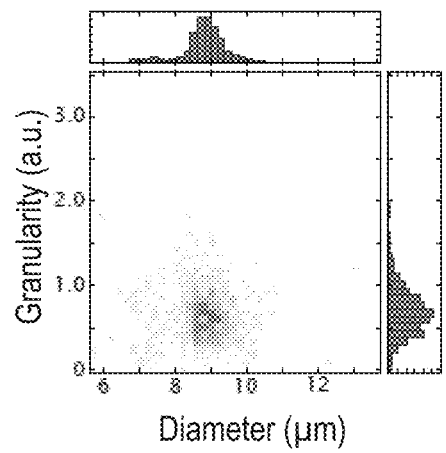
Figure 21C:
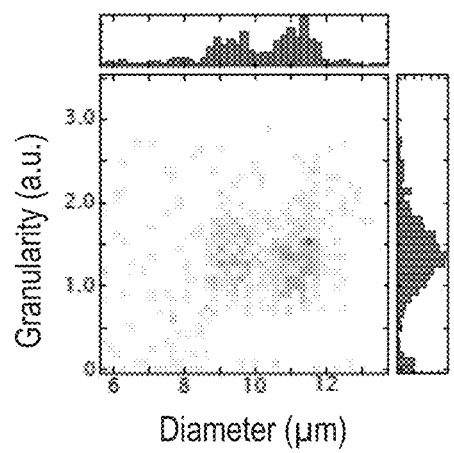

In an example embodiment, 2D histograms are constructed with on one axis the obtained diameter of the cell and on the other axis the obtained measure for granularity of the cell, wherein both the diameter and the granularity are obtained using methods and systems according to example embodiments In the example, illustrated in FIG. 21, for every leukocyte subtype a histogram is. made by plotting the cell diameter against the measure for granularity of the cell (corresponding with the internal complexity level). In the example the T-lymphocyte population, shown in FIG. 21A, is characterized by a cell diameter of 7.3784±0.44 μm. The majority of the lymphocytes, 81%, display a cell diameter within the 7-8 μm interval, separated from the significantly larger monocytes and granulocytes. With a cell diameter of 8.82±0.64 μm, 70% of the monocytes (FIG. 21B) can be found between 8.5-9.5 μm. The overall spread of the granulocyte population is fairly broad, and clearly divided into two distinct populations (FIG. 21C), pointing to a substantial level of cell activation present in the sample. Inadvertent granulocyte activation generated by subjecting the cells to purification protocols and acceleration levels typically utilized in density gradient centrifugation, has been documented and shown to induce changes in morphology. As activated cells are commonly characterized by an increase in size due to pseudopod formation, the granulocyte population on the left likely corresponds best to resting state, circulating granulocytes. By disregarding the cell with a diameter larger than 10.4%, this population is characterized by a diameter of 9.32-0.56 μm. 65% of these cell fall within 8.5=10 interval and 41% within the 8.5±9.5 μm, which is essentially superimposable onto the monocyte fraction (FIG. 21C).

The estimated cell diameters obtained using example embodiments disclosed herein may be in very agreement with previously reported sizes of leukocytes in suspension.

In example embodiments, granularity (i.e. the internal complexity) of the cells is used to discriminate between the monocyte and granulocyte populations. In the example illustrated in FIG. 21C it can be seen that the granulocyte fraction has a higher level of internal complexity, compared to the monocytes (FIG. 21B). This may be caused by the physiological function of granulocytes as vacuole-containing phagocytes. The lymphocyte population exhibits a more extensive level of internal complexity, which marginally overlaps with the granulocytes, but the clear size difference between these two populations allows unambiguous separation. Some embodiments enable the granularity of the cell and the cell size to be combined to discriminate between cell types. Every leukocyte subtype occupies a distinct region in the histogram, with limited overlap between different populations. Some embodiments enable the granularity and the cell size, obtained using method and systems according to example embodiments, to be sufficient to discriminate between granulocyte, monocyte and lymphocyte populations.

Figure 22:
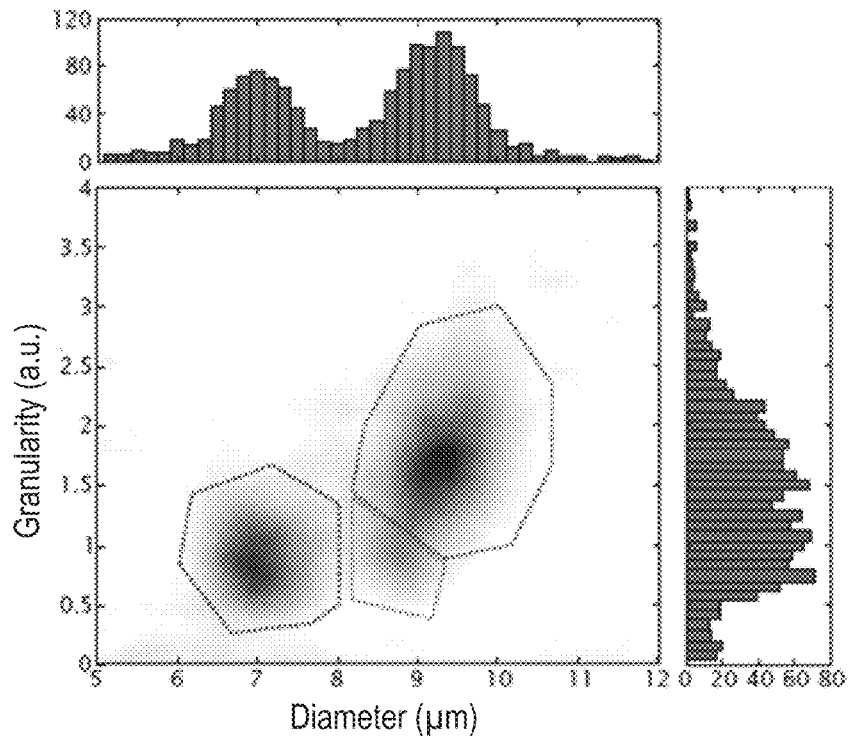
FIG. 22 shows the histograms of a whole blood analysis, according to example embodiments.

The ability of the lens-free imaging platform, according to example embodiments, to perform a 3-part leukocyte differential starting from a whole blood sample, using the morphological features previously singled out is additionally evaluated. A blood sample is divided into two aliquots immediately after drawing. One aliquot is analyzed on an inflow imaging system 200, in accordance with example embodiments, and the other is analyzed on a conventional hematology analyzer. The sample utilized on the lens-free imaging system 200, in accordance with an example embodiment, is minimally processed to lyse erythrocytes and reduce platelet contamination, and is subsequently run through the system 200 in five separate batches. For each batch 15,000 images are acquired at 50-150 fps and between 950-1800 cell holograms are selected, cleaned up and reconstructed, as previously described. The cell diameter and internal complexity is then determined using the recognition software developed in accordance with a method according to example embodiments, and the resulting histogram is plotted in FIG. 22. The scatter plot is based on the combined results of all five batches, and contains a total of 7,483 cells. The lymphocyte, monocyte and granulocyte fractions occupy distinct regions on the scatter plot, allowing them to be easily discriminated. In order to estimate total cell numbers and leukocyte subtype percentages, a region is manually defined for every type of leukocyte, similar to gating in a conventional flow cytometry scatter plot (FIG. 22). Cell counts and relative percentages of the whole blood sample for every batch, as well as the average and total cell count are summarized in the table shown below.

|  | Cell count | Lymph. (%) | Mono. (%) | Gran. (%) |
| --- | --- | --- | --- | --- |
| Ref. Values[37] | — | 20-40 | 4-8 | 41-70 |
| Test1 | 1776 | 37.3 | 9.0 | 53.7 |
| Test2 | 1695 | 27.7 | 7.0 | 65.3 |
| Test3 | 1624 | 32.2 | 7.8 | 60.0 |
| Test4 | 1434 | 37.5 | 6.8 | 55.7 |
| Test5 | 954 | 40.1 | 6.2 | 53.7 |
| Average | 1497 ± 329 | 35.0 ± 4.9 | 7.4 ± 1.1 | 57.7 ± 5.0 |
| Total | 7483 | 34.5 | 7.5 | 57.9 |
| BC LH-750 | — | 27.6 | 6.8 | 65.6 |

The table shows the cell count of the whole blood sample for every batch, the average count from the five batches, and the total count, all obtained through systems and methods according to example embodiments and the result from clinical lab performed on a Beckman Coulter LH-750 hematology analyzer.

Some embodiments enable the results of the lens-free-based classification method 100 and system 200 be in agreement with the outcome of a conventional 3-part leukocyte differential generated by a Beckman Coulter LH-750 hematology analyzer, as can be seen in the table.

Figure 23:
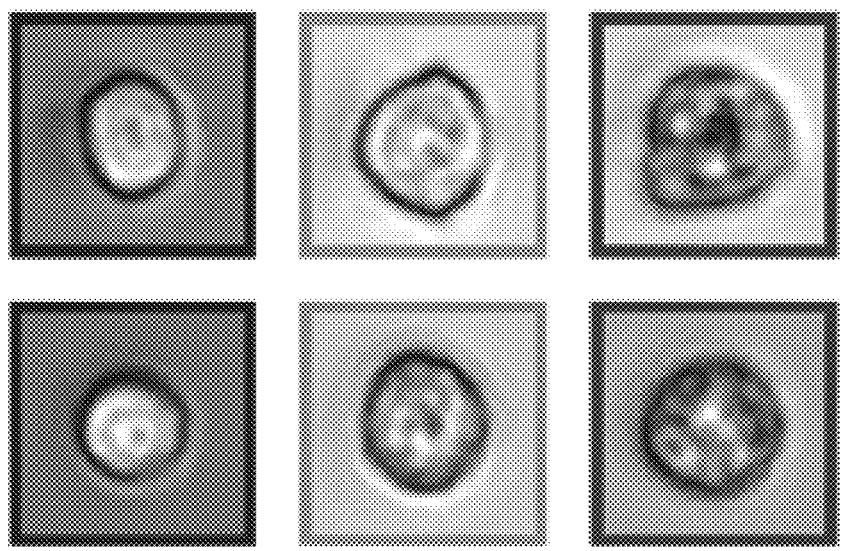
FIG. 23 depicts two cell images obtained through systems and methods from each of the three classification regions in FIG. 22, according to example embodiments (the left column shows lymphocytes, the middle column shows monocytes, and the right column show granulocytes).
Figure 13:
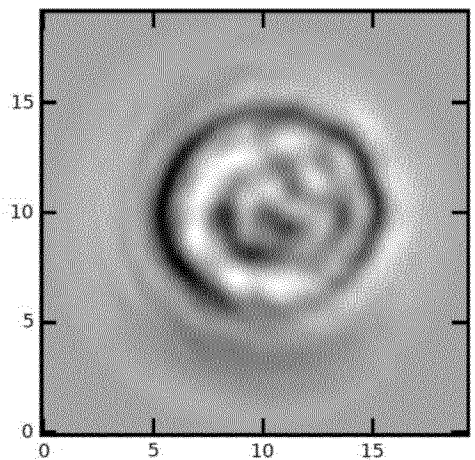
Figure 14:
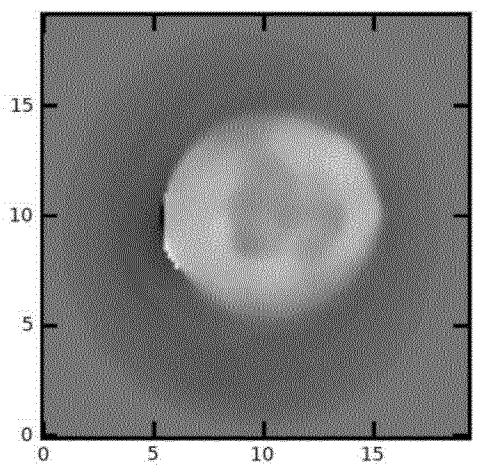

While their accuracies are comparable, the lens-free imaging system 200 may enable an availability of cell images post-analysis, unlike some conventional hematology analyzers. This feature allows the operator to interrogate images of outliers or particular data points within the classification and potentially gain a better understanding of the sample by examining the cell morphology detectable in the image. FIG. 23 depicts two cell images from each of the three classification regions in FIG. 22. The left column shows lymphocytes, the middle column shows monocytes, and the right column show granulocytes. Although the whole blood images are largely comparable to images of the corresponding purified leukocyte fractions (FIG. 21d), the morphology of the monocytes from the whole blood sample is noticeably different than that of the purified monocytes.

This morphological difference between purified and non-purified monocytes does not have consequences for the classification, as the cell edge is only used to calculate the cell size. However, it may provide direct access to the cell images used to build the classification, for further inspection when deemed necessary. The population of purified T-lymphocytes exhibit a higher level of internal complexity, characterized by an increase in the spread of the granularity (FIG. 22), when compared to whole blood lymphocytes which appear as a more homogenous and less internally complex population (FIG. 22). Sample preparation-induced morphological alterations are ubiquitous events in blood cell manipulations and systems 200 and methods 100 according to example embodiments may be able to recognize them.

In yet another aspect, the disclosure also relates to a system and method for irradiating a cell on a substrate, e.g. a cell in suspension in a microfluidic device. According to example embodiments, irradiation is performed using an optical chip with an embedded waveguide. The embedded waveguide thereby is positioned out of plane with respect to the substrate, by positioning the optical chip above the substrate in such a way that the edge of the optical chip, also forming an outcoupling edge of the waveguide, is facing the substrate. An example thereof, embodiments not being limited thereby, is shown in FIG. 2.

In still another aspect, the disclosure relates to a method and system, as described above, implemented as a computer-implemented invention in a processor and to corresponding processors.

One configuration of such a processor may for example include at least one programmable computing component coupled to a memory subsystem that includes at least one form of memory, e.g., RAM, ROM, and so forth. It is to be noted that the computing component or computing components may be a general purpose, or a special purpose computing component, and may be for inclusion in a device, e.g., a chip that has other components that perform other functions. Thus, one or more aspects of various embodiments can be implemented in digital electronic circuitry, or in computer hardware, firmware, software, or in combinations of them. For example, each of the method steps may be a computer implemented step. Thus, while a processor as such is prior art, a system that includes the instructions to implement aspects of the method as described above is not prior art.

Various embodiments also include a computer program product that provides the functionality of any of the methods according to example embodiments when executed on a computing device. In another aspect, the disclosure relates to a data carrier for carrying a computer program product as described above. Such a data carrier may comprise a computer program product tangibly embodied thereon and may carry machine-readable code for execution by a programmable processor. The disclosure thus relates to a carrier medium carrying a computer program product that, when executed on a computing device, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fiber optics, including the wires that comprise a bus within a computer.

The invention claimed is:

1. A method for recognizing a cell, comprising:
receiving an image of the cell, wherein receiving the image of the cell comprises reconstructing the image of the cell from a first hologram with its background removed;
performing edge detection on the reconstructed image of the cell;
detecting ridges within the reconstructed image of the cell; and
quantifying an internal complexity of the cell by gauging a contrast of the ridges with an average of a Laplacian on the detected ridges.

2. The method according to claim 1, further comprising:
performing a scale-space-based algorithm; and
characterizing, based on the scale-space-based algorithm, an edge and the internal complexity of the cell.

3. The method according to claim 2, wherein characterizing the internal complexity of the cell comprises characterizing a granularity of the cell.

4. The method according to claim 1, wherein performing edge detection comprises performing edge detection on the reconstructed image of the cell for defining an outline of the cell and for gauging a size of the cell.

5. The method according to claim 1, wherein receiving the image of the cell further comprises:
obtaining the first hologram, wherein the first hologram is a hologram of the cell with a background;
obtaining a second hologram, wherein the second hologram is a hologram without the cell; and
removing the background from the first hologram using the second hologram.

6. The method according to claim 5, wherein reconstructing the image of the cell comprises:
fitting a higher order polynomial with the background of the reconstructed image of the cell; and
removing the higher order polynomial from the reconstructed image of the cell.

7. The method according to claim 1, wherein the image of the cell is an image of a label-free cell.

8. The method according to claim 1, wherein the cell is a leukocyte, and wherein the method further comprises selecting, based on at least the detected ridges within the reconstructed image of the cell, a cell type for the reconstructed image of the cell from one of: a granulocyte, a monocyte, or a lymphocyte.

9. The method according to claim 8, wherein selecting the cell type is based on a combination of: results from the performed edge detection; the ridges detected; and the quantified internal complexity of the cell.

10. A system for recognition of a cell, comprising:
an input device arranged for receiving an image of the cell, wherein receiving the image of the cell comprises reconstructing the image of the cell from a first hologram with its background removed; and
a processor configured for:
performing edge detection on the reconstructed image of the cell;
detecting ridges within the reconstructed image of the cell; and
gauging contrast of the ridges with an average of a Laplacian on the detected ridges to quantify an internal complexity of the cell.

11. The system according to claim 10, wherein the processor is configured to:
perform a scale-space-based algorithm; and
characterize, based on the performed scale-space-based algorithm, an edge and the internal complexity or granularity of the cell.

12. The system according to claim 10, wherein the input device is an image recording device comprising:
a camera;
a microfluidic chip for guiding cells into a detection region of the camera;
a microfluidic chip holder for holding the microfluidic chip; and
a radiation source for stroboscopic illumination of the cells in the detection region.

13. The system according to claim 10, wherein the processor is further configured for identifying a cell type of the cell as a leukocyte based on at least the detected ridges within the reconstructed image of the cell, and wherein the cell is further a granulocyte, a monocyte, or a lymphocyte.

14. A non-transitory, computer-readable medium with instructions stored thereon, wherein the instructions, when executed by a processor, cause the processor to execute a method for recognizing a cell, comprising:
receiving an image of the cell, wherein receiving the image of the cell comprises reconstructing the image of the cell from a first hologram with its background removed;
performing edge detection on the reconstructed image of the cell;
detecting ridges within the reconstructed image of the cell; and
quantifying an internal complexity of the cell by gauging a contrast of the ridges with an average of a Laplacian on the detected ridges.

15. The non-transitory, computer-readable medium according to claim 14, wherein the method for recognizing the cell further comprises:
performing a scale-space-based algorithm; and
characterizing, based on the scale-space-based algorithm, an edge and the internal complexity of the cell.

16. The non-transitory, computer-readable medium according to claim 15, wherein characterizing the internal complexity of the cell comprises characterizing a granularity of the cell.

17. The non-transitory, computer-readable medium according to claim 14, wherein performing edge detection comprises performing edge detection on the reconstructed image of the cell for defining an outline of the cell and for gauging a size of the cell.

18. The non-transitory, computer-readable medium according to claim 14,
wherein receiving the image of the cell further comprises:
obtaining the first hologram, wherein the first hologram is a hologram of the cell with a background;
obtaining a second hologram, wherein the second hologram is a hologram without the cell; and
removing the background from the first hologram using the second hologram.

19. The non-transitory, computer-readable medium according to claim 18, wherein reconstructing the image of the cell comprises:
fitting a higher order polynomial with the background of the reconstructed image of the cell; and
removing the higher order polynomial from the reconstructed image of the cell.

20. The non-transitory, computer-readable medium according to claim 14, wherein the image of the cell is an image of a label-free cell.

* * * * *

UNITED STATES PATENT AND TRADEMARK OFFICE
CERTIFICATE OF CORRECTION

Page 1 of 2

PATENT NO. : 10,339,425 B2
APPLICATION NO. : 15/503764
DATED : July 2, 2019
INVENTOR(S) : Dries Vercruysse It is certified that error appears in the above-identified patent and that said Letters Patent is hereby corrected as shown below:

In the Drawings

Please replace FIGS. 13-14 with FIGS. 13-14 as shown on the attached page.

Signed and Sealed this
Twenty-fourth Day of September, 2019

Andrei Iancu
*Director of the United States Patent and Trademark Office*